United States Patent [19]

Schröder et al.

[11] 4,239,528
[45] Dec. 16, 1980

[54] PLANT GROWTH REGULATING COMPOSITIONS AND METHODS USING ALPHA-ISOCYANOCARBOXYLIC ACID COMPOUNDS

[75] Inventors: Rolf Schröder, Wuppertal; Klaus Lürssen, Berg. Gladbach, all of Fed. Rep. of Germany

[73] Assignee: Bayer Aktiengesellschaft, Leverkusen, Fed. Rep. of Germany

[21] Appl. No.: 955,436

[22] Filed: Oct. 27, 1978

[30] Foreign Application Priority Data

Nov. 19, 1977 [DE] Fed. Rep. of Germany ....... 2751782

[51] Int. Cl.$^3$ ............................................. A01N 37/34
[52] U.S. Cl. ........................................... 71/105; 71/70;
71/76; 71/77; 71/78; 71/DIG. 1; 260/464;
260/465 D; 260/465.4
[58] Field of Search ..................... 71/105, 70, 76, 106,
71/78; 260/464

[56] References Cited

U.S. PATENT DOCUMENTS

| | | | |
|---|---|---|---|
| 2,749,231 | 6/1956 | Ligett et al. .......................... 71/106 |
| 3,277,171 | 10/1966 | Hopkins .................................. 260/464 |
| 3,673,237 | 6/1972 | Janiak .................................... 71/106 |
| 3,773,824 | 11/1973 | Strong .................................... 71/106 |
| 4,083,863 | 4/1978 | Brand .................................... 260/464 |
| 4,098,600 | 7/1978 | Chupp .................................... 71/105 |
| 4,118,412 | 10/1978 | Cleare et al. .......................... 260/464 |

FOREIGN PATENT DOCUMENTS

2063502 4/1975 Fed. Rep. of Germany .......... 260/464
2349108 4/1975 Fed. Rep. of Germany .......... 260/464

OTHER PUBLICATIONS

Oediger et al., "Dialkylation in the presence, etc.," (1976) CA 84 No. 150239h. (1976).

*Primary Examiner*—Glennon H. Hollrah
*Attorney, Agent, or Firm*—Sprung, Felfe, Horn, Lynch & Kramer

[57] ABSTRACT

Alpha-isocyanocarboxylic acid compounds of the formula

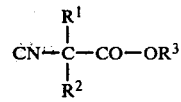

wherein $R^1$ and $R^2$, which can be identical or different, each represent hydrogen, alkyl, alkenyl, aryl, aralkyl or carbalkoxy or $R^1$ and $R^2$ together represent an alkylene chain with at least 2 carbon atoms and $R^3$ is hydrogen, alkyl, aryl, aralkyl or carbalkoxyalkyl, or, provided that $R^1$ and $R^2$ are both hydrogen, $R^3$ is an alkali metal ion, are outstandingly effective in plant growth regulant compositions, e.g., in growth inhibition stimulation or modification.

21 Claims, No Drawings

PLANT GROWTH REGULATING COMPOSITIONS AND METHODS USING ALPHA-ISOCYANOCARBOXYLIC ACID COMPOUNDS

The present invention relates to plant growth regulant compositions comprising certain α-isocyanocarboxylic acid compounds and, too, methods for regulating plant growth utilizing such compounds.

The use of α-isocyanocarboxylic acid derivatives as intermediate products in the pharmaceutical industry, for example for the preparation of amino acids, is known. See, e.g, German Offenlegungsschrift (German Published Specification) No. 2,063,502 and Japanese Patent Specification No. 74/043936.

Furthermore, it is known that trithiophosphoric acid S,S,S-trialkyl esters, for example, trithiophosphoric acid S,S,S-tri-n-butyl ester, have plant growth regulating properties (see U.S. Pat. Nos. 2,841,486 and 2,965,467). Such compounds can be used, for example, as active compounds for defoliating cotton. However, their action is not always completely satisfactory, especially in the case of low active compound concentrations and applications.

It is also already known that 2-halogenoethane-sulphinic acids, for example, 2-chloroethanesulphinic acid, and their derivatives can be used as plant growth regulators, from German Offenlegungsschrift (German Published Specification) No. 2,110,773. However, their action is not always completely satisfactory, especially in the case of low application amounts.

Furthermore, it is known that "Off-Shoot-T" (a commercially available product based on fatty alcohols with 6, 8, 10 and 12 carbon atoms) exhibits a plant growth regulating action (see Farm. Chem. Handbook, 1975, Meister Publishing Co., Willoughby, Oh. 1975 and Pesticide Dictionary D 147). However, the action is also not always completely satisfactory, especially at low active compound concentrations and dosages.

It has now been found that the α-isocyanocarboxylic acid derivatives of the formula

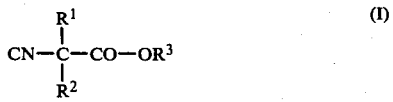

wherein $R^1$ and $R^2$, which can be identical or different, each are hydrogen, alkyl, alkenyl, aryl, aralkyl or carbalkoxy or $R^1$ and $R^2$ together represent an alkylene chain with at least 2 carbon atoms and $R^3$ is hydrogen, alkyl, aryl, aralkyl or cabalkoxyalkyl or, provided that $R^1$ and $R^2$ denote hydrogen, $R^3$ is is an alkali metal ion, have powerful plant growth regulating properties.

Accordingly, the present invention provides a plant-growth-regulating composition containing as active ingredient a compound of the formula (I) in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the formula (I) alone or in the form of a composition containing as active ingredient a compound of the formula (I) above, in admixture with a diluent or carrier.

Some of the compounds which can be used according to the invention also possess a herbicidal activity.

Surprisingly, the α-isocyanocarboxylic acid derivatives of the formula (I) which can be used according to the invention exhibit a considerably more powerful plant growth regulating action than the substances known from the state of the art, that is to say trithiophosphoric acid S,S,S-tri-n-butyl ester, 2-chloroethanesulphinic acid and Off-Shoot-T, which are active compounds of high activity and the same type of action. The substances which can be used according to the invention thus represent a valuable enrichment of the art.

The formula (I) provides a general definition of the isocyanocarboxylic acid derivatives to be used according to the invention. Preferably, in the formula (I):

$R^1$ and $R^2$, which can be identical or different, each represent hydrogen, straight-chain or branched alkyl with 1 to 6 (especially 1 to 4) carbon atoms, straight-chain or branched alkenyl with 2 to 6 (especially 2 to 4) carbon atoms (allyl being mentioned in particular), aryl with 6 or 10 carbon atoms, aralkyl with 6 or 10 carbon atoms in the aryl part and 1 to 4 carbon atoms in the alkyl part, or carbalkoxy with 1 to 4 carbon atoms in the alkoxy part (carbomethoxy and carbethoxy being mentioned in particular) or $R^1$ and $R^2$ together represent an alkylene chain with 2 to 7 (especially 2 to 5) carbon atoms and $R^3$ represents hydrogen, straight-chain or branched alkyl with 1 to 20 (especially 1 to 16) carbon atoms, aryl with 6 or 10 carbon atoms, aralkyl with 6 or 10 carbon atoms in the aryl part and 1 to 4 carbon atoms in the alkyl part, carbalkoxyalkyl with 1 to 4 carbon atoms in each alkyl group, or, provided that $R^1$ and $R^2$ represent hydrogen, a sodium ion or potassium ion.

Examples which may be mentioned of compounds of the formula (I) are: α-isocyano-acetic acid, -propionic acid, -butyric acid, -valeric acid and -caproic acid, α-isocyano-α-methyl-propionic acid and -butyric acid, α-isocyano-α-ethylbutyric acid, α-isocyano-α-methyl-, -α-ethyl-, -α-n-propyl- and -α-iso-propyl-valeric acid, α-isocyano-α-methyl-, -α-ethyl-, -α-n-propyl-, -α-iso-propyl-, -α-n-butyl-, -α-isobutyl-, -α-sec.-butyl- and -α-tert.-butyl-caproic acid, α-isocyano-α-benzylpropionic acid, 1-isocyano-1-cyclopropane-carboxylic acid, α-isocyano-α-allyl-propionic acid, α-isocyano-β-methyl-butyric acid, α-isocyano-α,β-dimethyl-butyric acid, α-isocyano-α-carbomethoxymethyl- and α-isocyano-α-carbethoxymethyl-propionic acid, and furthermore the corresponding methyl, ethyl, n-propyl, isopropyl, n-butyl, isobutyl, sec.-butyl, tert.-butyl, n-pentyl, n-hexyl, n-octyl, n-nonyl, n-decyl, n-dodecyl, tetradecyl, benzyl, carbomethoxymethyl or carbethoxymethyl ester, and the sodium salt and potassium salt of α-isocyanoacetic acid.

Some of the isocyanocarboxylic acid derivatives of the formula (I) which can be used according to the invention are known [see Chem. Ber. 109, (1976), page 482 et seq.; J. Org. Chem. 30 (1965), pages 1905-7; German Offenlegungsschrift (German Published Specification) No. 2,063,502; Japanese Patent Specification No. 74 043936; Liebigs Ann. Chem. 1973, pages 611-18; Japanese Patent Specifications Nos. 50-121245; 74-027860; and 49-066649; German Offenlegungsschrift (German Published Specification) No. 1,962,898; Tetrahedron Lett. 1969, pages 5091-4; Chem. Commun. 1969. pages 811-2; Angew. Chem. 83 (1971), pages 357-8; and Bull. Chem. Soc. Jap. 44, (1971) pages 1407-10]. Individual examples of the active compounds according to the invention are new, but they can be prepared in a simple manner by known processes.

For example, the salts of α-isocyanoacetic acid are obtained by reacting isocyanoacetic acid esters of the formula

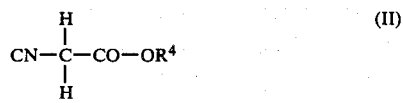

wherein
R⁴ denotes methyl or ethyl,
with alkali metal hydroxides, such as sodium hydroxide or potassium hydroxide, at temperatures between 0° C. and 20° C. in the presence of a solvent or diluent, and subsequently filtering the mixture.

The esters of the α-isocyano-carboxylic acids with longer-chain alcohols are obtained, for example, when methyl or ethyl esters of the corresponding acids are reacted with the relevant alcohols at temperatures between 0° C. and 150° C. in the presence of a base and of a solvent.

The methyl and ethyl esters, required as starting materials, of the α-isocyanocarboxylic acids are known, or they can be prepared by processes which are known in principle (see Angew. Chemie 77, (1965) page 492 and Chem. Ber. 108, (1975), page 1580).

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and gassing. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The active compound concentrations can be varied within a substantial range. In general 0.01 to 50 kg, preferably 0.05 to 10 kg, of active compound are employed per hectare of soil surface.

The present invention also provides plants, the growth of which has been regulated by their being grown in areas in which immediately prior to and/or during the time of the growing a compound of the formula (I) was applied, alone or in admixture with a diluent or carrier.

It will be seen that the usual methods of providing a harvested crop may be improved by the present invention.

The Examples which follow illustrate the activity of the substances according to the invention as growth regulators without excluding the possibility of further applications as growth regulators.

In these Examples, the compounds according to the present invention are each identified by the number (given in brackets) of the corresponding preparative Example, which will be found later in this specification.

The known comparison compounds are identified as follows:

(A)=$(CH_3-CH_2-CH_2-CH_2-S)_3PO$ (tri-n-butyl-trithiophosphoric acid ester)

(B)=

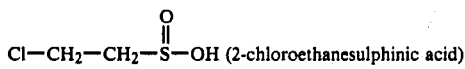
 (2-chloroethanesulphinic acid)

(C) = Off-Shoot-T (a plant growth regulator based on fatty alcohols with 6, 8, 10 and 12 carbon atoms).

EXAMPLE A

Defoliation of cotton plants and desiccation of cotton leaves

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 1 week, the shedding of leaves and the desiccation of the leaves was rated. The results were compared with those of the untreated control plants.

In this test, compound (1) caused substantially greater shedding of leaves and greater desiccation of the leaves than substance (A), known from the prior art.

EXAMPLE B

Inhibition of growth of side shoots of tobacco

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tobacco plants were grown in a greenhouse until the 7th foliage leaf had unfolded. In this stage, the apical vegetative tips of the plants were removed and the plants were sprayed with the formulations of active compound until dripping wet. After 3 weeks, the side shoots of the plants were broken off and weighed. The weight of the side shoots of the treated plants was compared with that of the untreated control plants.

In this test, compound (1) caused substantially better inhibition of the growth of side shoots than substance (C), known from the prior art.

EXAMPLE C

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth of the treated plants was compared with the additional growth of the untreated control plants.

In this test, compounds (4), (5), (6), (11), (23), (25), (26) and (32) caused a substantially greater inhibition of growth than substance (B), known from the prior art.

EXAMPLE D

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the treated plants was compared with the additional growth of the untreated control plants.

In this test, compounds (1), (4), (5) and (12) caused a substantially greater inhibition of growth than substance (B), known from the prior art.

EXAMPLE E

Inhibition of growth of wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Wheat plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, compounds (1), (5) and (8) caused a substantially greater inhibition of growth than substance (B), known from the prior art.

EXAMPLE F

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Barley plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, compounds (1), (5), (11) and (32) caused a substantially greater inhibition of growth than substance (B), known from the prior art.

EXAMPLE G

Promotion of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the treated plants was compared with the additional growth of the untreated control plants.

In this test, compound (6) greatly promoted growth.

PREPARATIVE EXAMPLES

EXAMPLE 1

$$CN-CH_2-CO-O^{\ominus}K^{\oplus} \quad (1)$$

A solution of 61.5 g (1.1 mol) of potassium hydroxide in 500 ml of ethanol was added dropwise to a solution of 113 g (1 mol) of α-isocyanoacetic acid ethyl ester in 750 ml of ether at about 5° C. in the course of 30 minutes, whilst cooling and stirring. The mixture was then subsequently stirred at about 2°–10° C. for a further 4 hours and filtered off and the residual traces of solvent were removed in vacuo in a desiccator. 117 g (95% of theory) of the potassium salt of α-isocyanoacetic acid were isolated in the form of a white powder with a melting point of 210° C. (decomposition).

EXAMPLE 2

$$\underset{\underset{\displaystyle}{|}}{CN-CH-CO-OC_8H_{17}} \quad (2)$$
$$\overset{CH_3}{}$$

0.12 g (5 mmol) of sodium hydride was added to a solution of 6.3 g (50 mmol) of α-isocyanopropionic acid ethyl ester and 6.5 g (50 mmol) of octanol in 150 ml of toluene (analytical grade). 50 ml of solvent were then distilled off under normal pressure, the reaction mixture was allowed to cool and 100 ml of water were added. After separation of the phases, the organic phase was dried over magnesium sulphate and filtered and the toluene was distilled off in vacuo in a rotary evaporator. 10.2 g (97% of theory) of α-isocyano-propionic acid octyl ester remained in the form of a yellow liquid having a refractive index $n_D^{23}$ of 1.4439.

The compounds of the formula $$\underset{\underset{\displaystyle R^2}{|}}{\overset{\overset{\displaystyle R^1}{|}}{CN-C-CO-OR^3}} \quad (I)$$

listed in the table which follows were prepared analogously to Example 1 or 2:

| Example No. | R[1] | R[2] | R[3] | Yield (% of theory) | Melting point; refractive index; boiling point [°C./mm Hg] |
|---|---|---|---|---|---|
| 3 | H | H | Na | 89 | 220 (decomposition) |
| 4 | CH_3 | CH_3 | C_2H_5 | 99 | 47/6 |
| 5 | H | H | CH_3 | 88 | 44/1 |
| 6 | H | H | ⟨phenyl⟩—CH_2— | 68 | 130/0,9 |
| 7 | C_3H_7-iso | H | C_2H_5 | 70 | 70/3 |
| 8 | CH_3 | CH_2=CH—CH_2— | C_2H_5 | 92 | 85/10 |
| 9 | CH_3 | ⟨phenyl⟩—CH_2 | C_2H_5 | 99 | $n_D^{20}$:1,5089 |
| 10 | CH_3 | C_3H_7-iso | C_2H_5 | 78 | 80/10 |
| 11 | CH_3 | CO—OC_2H_5 | C_2H_5 | 92 | $n_D^{20}$:1,4260 |
| 12 | H | H | —CH_2—CO—OC_2H_5 | 98 | $n_D^{20}$:1,4418 |
| 13 | CH_3 | CH_3 | C_{10}H_{21} | 91 | $n_D^{20}$:1,4440 |
| 14 | CH_3 | CH_3 | C_8H_{17} | 84 | $n_D^{20}$:1,4507 |
| 15 | CH_3 | CH_3 | C_{12}H_{25} | 90 | $n_D^{20}$:1,4926 |
| 16 | CH_3 | CH_3 | C_{14}H_{29} | 91 | $n_D^{20}$:1,4530 |
| 17 | CH_3 | H | C_{10}H_{21} | 82 | $n_D^{20}$:1,4502 |
| 18 | CH_3 | H | C_{12}H_{25} | 90 | $n_D^{20}$:1,4565 |
| 19 | CH_3 | H | C_{14}H_{29} | 94 | $n_D^{20}$:1,4520 |
| 20 | H | H | C_8H_{17} | 89 | $n_D^{20}$:1,4466 |
| 21 | C_3H_7-iso | H | C_8H_{17} | 90 | $n_D^{20}$:1,4441 |
| 22 | C_3H_7-iso | H | C_{10}H_{21} | 89 | $n_D^{20}$:1,4480 |
| 23 | C_3H_7-iso | H | C_{12}H_{25} | 88 | $n_D^{20}$:1,4515 |
| 24 | C_3H_7-iso | H | C_{14}H_{29} | 89 | $n_D^{20}$:1,4535 |
| 25 | —CH_2—CH_2— | | C_8H_{17} | 90 | $n_D^{20}$:1,4559 |
| 26 | —CH_2—CH_2— | | C_{10}H_{21} | 84 | $n_D^{20}$:1,4535 |
| 27 | —CH_2—CH_2— | | C_{12}H_{25} | 86 | $n_D^{20}$:1,4545 |
| 28 | —CH_2—CH_2— | | C_{14}H_{29} | 80 | $n_D^{20}$:1,4531 |
| 29 | CH_3 | CH_3 | CH_3 | 80 | $n_D^{20}$:1,4769 |
| 30 | CH_3 | CH_3 | ⟨phenyl⟩—CH_2— | 80 | $n_D^{20}$:1,5129 |
| 31 | —CH_2—CH_2— | | ⟨phenyl⟩—CH_2— | 96 | $n_D^{20}$:1,5109 |
| 32 | —CH_2—CH_2— | | CH_3 | 81 | $n_D^{20}$:1,4450 |

| Example No. | R¹ | R² | R³ | Yield (% of theory) | Melting point; refractive index; boiling point [°C./mm Hg] |
|---|---|---|---|---|---|
| 33 | CH₃ | CH₃ | —CH₂—CO₂CH₃ | 99 | $n_D^{20}$:1,4271 |

It will be understood that the specification and examples are illustrative but not limitative of the present invention and that other embodiments within the spirit and scpoe of the invention will suggest themselves to those skilled in the art.

What is claimed is:

1. Plant growth regulating composition containing as active ingredient, in an effective amount to regulate plant growth, an α-isocyanocarboxylic acid compound of the formula

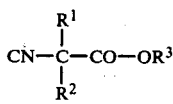

wherein
R¹ and R² together represent an alkylene chain with 2 to 5 carbon atoms and
R³ is hydrogen, alkyl of up to 20 carbon atoms, aryl of 6 or 10 carbon atoms, aralkyl of 6 or 10 carbon atoms in the aryl moiety and 1 to 4 carbon atoms in the alkyl moiety, or carbalkoxyalkyl of 1 to 4 carbon atoms in each alkyl moiety
in admixture with a solid or liquefied gaseous diluent or carrier or in admixture with a liquid diluent or inert carrier containing a surface active agent.

2. Plant growth regulating composition as claimed in claim 1 wherein R¹ and R² together are alkylene of 2 carbon atoms.

3. Plant growth regulating composition as claimed in claim 1 wherein R³ is hydrogen.

4. Plant growth regulating composition as claimed in claim 1 wherein R³ is alkyl of 1 to 16 carbon atoms.

5. Plant growth regulating composition as claimed in claim 1 wherein R³ is phenyl.

6. Plant growth regulating composition as claimed in claim 1 wherein R³ is benzyl.

7. Plant growth regulating composition as claimed in claim 1 wherein R³ is carbalkoxyalkyl of from 1 to 4 carbon atoms in each alkyl moiety.

8. Plant growth regulating composition as claimed in claim 1 wherein said compound is 1-isocyanocyclopropyl carboxylic acid octyl ester.

9. Plant growth regulating composition as claimed in claim 1 wherein said compound is 1-isocyanocyclopropyl carboxylic acid benzyl ester.

10. Plant growth regulating composition as claimed in claim 1 wherein said compound is 1-isocyanocyclopropyl carboxylic acid methyl ester.

11. Plant growth regulating composition as claimed in claim 1 wherein said α-isocyanocarboxylic acid compound constitutes from 0.1 to 95% of said composition.

12. Method of regulating plant growth, which method comprises applying to plants, or their habitat, a plant growth regulatingly effective amount of an α-isocyanocarboxylic acid compound of the formula

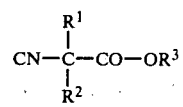

wherein
R¹ and R² together represent an alkylene chain with 2 to 5 carbon atoms and
R³ is hydrogen, alkyl of up to 20 carbon atoms, aryl of 6 or 10 carbon atoms, aralkyl of 6 or 10 carbon atoms in the aryl moiety and 1 to 4 carbon atoms in the alkyl moiety, or cycloalkyl of 1 to 4 carbon atoms in each alkyl moiety
in admixture with a solid or liquefied gaseous diluent or carrier or in admixture with a liquid diluent or carrier containing a surface active agent.

13. Method as claimed in claim 12 wherein R¹ and R² together are alkylene of 2 carbon atoms.

14. Method as claimed in claim 12 wherein R³ is hydrogen.

15. Method as claimed in claim 12 wherein R³ is alkyl of 1 to 16 carbon atoms.

16. Method as claimed in claim 12 wherein R³ is phenyl.

17. Method as claimed in claim 12 wherein R³ is benzyl.

18. Method as claimed in claim 12 wherein R³ is carbalkoxyalkyl of from 1 to 4 carbon atoms in each alkyl moiety.

19. Method as claimed in claim 12 wherein said composition is selected from 1-isocyanocyclopropyl carboxylic acid octyl ester, 1-isocyanocyclopropyl carboxylic acid decyl ester, 1-isocyanocyclopropyl carboxylic acid benzyl ester or 1-isocyanocyclopropyl carboxylic acid methyl ester.

20. Method as claimed in claim 12 wherein said composition is applied to an area of plant cultivation in an amount of 0.01 to 50 kg/hectare.

21. Method as claimed in claim 12 wherein said composition is applied to an area of plant cultivation in an amount of 0.05 to 10 kg/hectare.

* * * * *